United States Patent
Bonham

(10) Patent No.: US 7,077,833 B2
(45) Date of Patent: Jul. 18, 2006

(54) CONVENIENT UROLOGY UNDERGARMENT PANT SYSTEM FOR URINE COLLECTION

(75) Inventor: Celeste V. Bonham, Malibu, CA (US)

(73) Assignee: URO Concepts Inc., Malibu, CA (US)

( * ) Notice: Subject to any disclaimer, the term of this patent is extended or adjusted under 35 U.S.C. 154(b) by 114 days.

(21) Appl. No.: 10/839,422

(22) Filed: May 3, 2004

(65) Prior Publication Data

US 2005/0075615 A1  Apr. 7, 2005

Related U.S. Application Data

(60) Provisional application No. 60/509,644, filed on Oct. 7, 2003.

(51) Int. Cl.
*A61F 5/44* (2006.01)
*A61M 1/00* (2006.01)

(52) U.S. Cl. .................. 604/327; 604/323; 604/349; 604/353

(58) Field of Classification Search ............. 604/327, 604/329, 343, 349–353
See application file for complete search history.

(56) References Cited

U.S. PATENT DOCUMENTS

| | | | |
|---|---|---|---|
| 3,547,123 A | 12/1970 | Sachs | |
| 4,511,358 A | 4/1985 | Johnson, Jr. et al. | |
| 4,553,968 A | 11/1985 | Komis | |
| 4,644,945 A | 2/1987 | Thorner | |
| 4,846,816 A * | 7/1989 | Manfredi | 604/323 |
| 5,009,649 A | 4/1991 | Goulter et al. | |
| 5,032,118 A | 7/1991 | Mason | |
| 5,057,094 A | 10/1991 | Abbey | |
| 5,133,923 A | 7/1992 | Klug | |
| 5,161,257 A * | 11/1992 | Arensdorf et al. | 2/465 |
| 5,271,101 A | 12/1993 | Speth et al. | |
| 5,787,512 A | 8/1998 | Knox | |
| 5,935,116 A * | 8/1999 | Kristensen | 604/353 |
| 6,007,524 A | 12/1999 | Schneider | |
| 6,419,665 B1 | 7/2002 | Cohen | |

* cited by examiner

Primary Examiner—Tatyana Zalukaeva
Assistant Examiner—Melanie J Hand

(57) ABSTRACT

A convenient urology undergarment pant system for collecting urine discharge comprising of an undergarment that extends from around the waist and down the thighs. The undergarment can be used with urine collection devices from the urethra area (male condom-like coupling or female external receiving device), from the bladder by means of an ileoconduit system, and from the kidney(s) by means of a nephrostomy system. The undergarment includes a sewn inner pouch formed from an additional piece of fabric that holds the leg bag in place without the need for leg straps. There is an opening in the crotch area of the undergarment that provides means for placing the leg bag inside the inner pouch. The undergarment also includes a lower opening to accommodate the release valve of the leg bag.

20 Claims, 3 Drawing Sheets

CONVENIENT UROLOGY UNDERGARMENT PANT SYSTEM FOR URINE COLLECTION

CROSS REFERENCE

This application is related to U.S. Provisional Patent Application No. 60/509,644, filed Oct. 7, 2003, now expired.

FIELD OF INVENTION

This invention relates to an undergarment pant system containing an external collection urology system. This undergarment pant system contains an internal leg pouch that conceals and securely holds the external collection system in place without the need for leg straps to hold the leg bag in place. This invention is used with external collection systems including those using condom, ileoconduit and nephrostomy systems.

BACKGROUND OF INVENTION

This invention relates generally to the field of urology and urinary incontinence for external collection systems using a condom or female device appliance for collecting urine through the urethra. This undergarment pant is an improvement from the existing systems of securely holding the leg bag in place without the need of leg straps. Most current systems are held on the lower extremity by means of leg straps connected to the upper and lower part of the leg bag. Leg straps must be tightly attached to the leg to avoid the leg bag from dropping down the leg when the leg bag is filled and heavy. This tightness around the lower extremity can cause constriction to the circulation to the lower portion of leg. In addition, the undergarment pant system as disclosed in this specification gives the user a convenient means for drainage of urine from the leg bag without the need of disengaging the leg bag from the user's leg. The present invention offers the user a higher degree of comfort while using an external collection system.

This invention can also be used for persons, both male and female, having bladder disease that causes an obstruction of elimination of fluid from the bladder and using an ileoconduit system. The ileoconduit system includes a tube inserted through the abdomen into the bladder for external drainage of fluid into a leg bag. Our system can also be used for persons, both male and female, having kidney disease that causes an obstruction of elimination of fluid from the kidney(s) and using a nephrostomy system. A nephrostomy system includes a tube inserted through the back into the kidney(s) that allows for drainage of fluid into a leg bag.

For the ambulatory person diagnosed with urinary incontinence, this system offers the user a higher degree of physical activity and a more active lifestyle.

In addition to ambulatory persons, paraplegic, quadriplegic and non-ambulatory persons using external collection systems can wear the undergarment pant.

Further, persons performing activities where urine elimination is restricted, limited or eliminated can also wear the undergarment pant system.

BACKGROUND—DISCUSSION OF PRIOR ART

This invention addresses the problems associated with persons who are diagnosed with urology diseases or illnesses that have symptoms of urinary incontinence or bladder and kidney malfunctions. This undergarment pant offers an improved system for external collection urology systems, including condom, ileoconduit and nephrostomy. This system offers the user a higher degree of comfort compared to systems currently available. It offers the user the ability to wear the external collection system without the need of leg straps that can cause constriction of circulation to the lower extremity.

Many persons who suffer from urology problems and urinary incontinence may be limited with physical activities. The symptoms of incontinence can negatively affect the lifestyle of a person, including social, exercise and sports activities. The undergarment pant offered here, when worn with an external collection system, will offer a higher level of physical activity without the fear of the leg bag falling down the leg, thereby disengaging the collection system and causing a urinary mishap. This undergarment pant, when worn with an external collection system, will help to protect against a urinary mishap since it completely houses the condom external collection system; and it houses the tubing and leg bag of the ileoconduit and nephrostomy external collection systems.

The medical and urology industries, as well as the general public, consider incontinence a handicap. It is important that incontinence begins to be viewed as a more socially acceptable diagnosis. It is equally important to discover ways to help those suffering from incontinence to lead a more normal lifestyle. There is a broad range of conditions and medical disorders that can cause someone to have a weakening of the bladder and/or kidney and become incontinent. Some of these conditions and disorders include aging, birth defects, pelvic surgery, spinal cord injuries, multiple sclerosis, kidney stones and neurological diseases. For women, a common reason for stress incontinence may occur after multiple childbirths and menopause. Stress incontinence occurs when the sphincter or pelvic muscles have been damaged or weakened which causes urinary leakage due to pressure on the bladder.

In the United States, approximately 25 million men, women and children suffer varying degrees of urinary incontinence. No particular age group or gender is eliminated from being diagnosed with incontinence. Statistics show approximately eighty percent (80%) of those experiencing incontinence are females. It is further estimated that one in four women ages 30–59 have had an episode of urinary incontinence. Older demographics of the population are highly affected but young people are also affected, including athletics, new mothers, and those suffering from an illness, birth defect, or physical trauma (surgery or spinal cord injury).

The 2000 U.S. Census estimated the population between 45 and 85 year of age at 92,705,000 people (33.1% of the U.S. population). Those between the ages of 45 and 64 were estimated at 61,953,000 (22.2%). The Census estimated males over 65 at 14,410,000 (5.1%). Statistics show 5% of men 64 years of age and younger, and up to 15% of men over 64 years of age experience bladder leakage. Based on these numbers, it is estimated 2.2 million men over the age of 65 have experienced bladder leakage.

The aging population of Baby Boomers, those born between 1946 and 1964; ages 39 to 57, are shown by the Census Bureau to be estimated at 74.7 million people. The Pre-Boomers (58 and older) are estimated at 64.4 million. Baby Boomers are a growing and largely underserved population. Typically, Baby Boomers have lead an active lifestyle including sports, active social and work activities. Baby Boomers are also statistically living longer and healthier lives. Baby Boomers and Pre-Boomers would choose a more active lifestyle if they are physically and mentally capable.

An incontinent person may become worried that they could have an accident in public and their condition would be discovered. They may also feel ashamed because they are unable to function normally by loss of control of their bladder. The stigma connected to incontinence includes 'wetting pants' or 'wearing diapers'. An incontinent person may have low self-esteem and fear ridicule and avoid social contact and become isolated.

The devices and products currently available for urinary incontinence may reduce the options for an incontinent person to participate in social, exercise and sports activities. An incontinent person wants as "normal" of lifestyle as they are physically and mentally capable of achieving. This disclosed undergarment pant system, when worn with an external collection urology system, offers another choice for those suffering from urinary incontinence to have the ability to participate more freely in a social and physical lifestyle.

SUMMARY OF THE INVENTION

The disclosed undergarment pant is an improved system for those wearing external collection urology systems since it does not require the use of leg straps. This undergarment pant holds the urine leg bag in place through the use of an inner pocket or pouch sewn in one or both leg of the undergarment pant. This eliminates the need of leg strays to hold the urine leg bag. It also gives further support of the urine collection system during physical activities, and keeps the leg bag from falling down the leg that can cause an accident or leakage. Sewing the inner leg pouch to structural seams in the undergarment pant gives it added support. When the leg bag is filled with urine it can become very heavy and may increase the possibility of the leg bag dropping down the leg and causing an accident or leakage. If the leg straps are very tight, this can restrict circulation to the lower extremity. Even minor restriction can contribute to a medical condition for people suffering from diabetes, high blood pressure, poor circulation and those confined to wheelchairs. This disclosed undergarment pant eliminates the need for any leg straps. In addition, the disclosed undergarment pant is very comfortable to wear and does not constrict circulation to the lower extremity.

The disclosed undergarment pant is an improved system for those wearing external collection urology systems since the whole external collection urology system (condom/female device, tubing, leg bag) are all contained within the structure of the undergarment pant. The undergarment pant holds the external collection urology system in place even during physical activity.

For many suffering from incontinence, the ability to play sports or exercise can be compromised and negatively affected due to the possibility of having a urinary accident or leakage. Going to the gym and participating in an aerobics exercises, treadmill or stair climber is considered impossible or risky by many who suffer from incontinence due to the potential embarrassment of having a urinary accident. The current three leading personal sport activities in the United States are running, golf and tennis. Of these, approximately 75% of golfers are men; tennis and running are nearly equally divided with tennis 51.1% men and running 53.9% men (American Sports Data). Outdoor sports such as fishing, rafting, hunting or camping can be difficult or considered impossible for those who are suffering from urinary incontinence due to the possibility of having a urinary accident or leakage.

The disclosed undergarment pant system will allow people with incontinence to participate in more social and sports activities such as playing golf, tennis, jogging, walking and interaction with the world with more confidence from urinary leakage and accidents. The undergarment pant is constructed be means of utilizing the structural seams to further support the inner pouch when a leg bag is placed in the pouch. The stretchable fabric further helps to keep the proper fit against the body and further helps to keep the external collection urology system in place.

Many persons using diapers for urine collection choose not to participate in some social and physical activities due to the possible leakage, accidents and odor. In some cases, if the diapers are not changed often, the diaper may droop due to the weight of the urine collection and may cause an accident or leakage. This disclosed undergarment pant will offer another system than wearing diapers thereby giving the user more confidence in participating in social and physical activities without being embarrassed by urinary leakage or odor.

For men, the external condom catheter urology collection system is an alternative to wearing diapers and may be considered more effective than diapers for urine collection during physical and social activities. The condom-type of external collection systems consist of a means for receiving the urine through a condom, transporting the urine through a tube and collecting the urine in a leg bag attached to the leg by leg straps or to the side of the bed. The male external catheter condom system offers many men a more normal lifestyle, both professionally and personally, compared to having to wear diapers. Some male external condom systems include means for keeping the condom in place by adhesives (U.S. Pat. No. 3,739,783; RE33,206; U.S. Pat. No. 4,187,851) or a support device (U.S. Pat. No. 5,797,890).

Due to physiology differences of men and women, there are fewer choices for effective external collecting systems for female users. Some of the existing external collection systems for women use adhesives (U.S. Pat. Nos. 4,904,248; 4,484,917; 4,568,339), vacuum seal (U.S. Pat. No. 4,795,449) or bellows (U.S. Pat. Nos. 4,681,572; 4,889,532).

Most external urine collection systems are ineffective for many physical activities. During physical activities, like jogging, tennis and aerobics, the urine-holding bag strapped to the leg does not always stay in place. Leg bags may hold 500 ml (2 cups) or 1000 ml (4 cups) of urine when full. The weight of a full, or nearly full leg bag restricts activities of the user since the leg straps may not hold the leg bag in place during these physical activities. If the leg bag drops down the leg the user has the risk the tubes will become unattached to the collection system and cause an accident. In additional to the conventional leg straps to hold the urine bag on the leg, there are harness waist systems (U.S. Pat. Nos. 4,511,358; 4,846,816) that include a bag held to the leg by straps on the bottom and straps connected to a waistband.

The urine collection system disclosed in this application includes an undergarment pant made from stretchable fabric. There are other urine collection systems that include garments. Some include an opening in the undergarment for the male penis to be placed through and attached to an external condom system with leg bag (U.S. Pat. Nos. 4,713,066; 4,553,968). One prior art urine collection system using a pant garment and a pocket is disclosed in U.S. Pat. No. 5,032,118. However, this disclosed device has a number of shortcomings.

Their pocket for holding the leg bag is positioned outside the garment and extends below the lower edges of the garment. For the urine collection system (condom sheath, tubing and leg bag) to be fully assembled, the tubing must be placed through a hole that leads to the outside of the garment, thereby positioning the tubing on the outside of the garment so that it can be attached to the leg bag located in the pocket on the outside of the garment.

There are brief undergarment systems (U.S. Pat. Nos. 6,007,524; 5,009,649) and boxer short undergarment systems (U.S. Pat. Nos. 3,547,123; 6,419,665) with connecting fluid reservoirs contained within the undergarments. There is a boxer short undergarment system that contains a liquid-proof pocket (U.S. Pat. No. 4,644,945) to receive urine leakage from the penis. There is also an outer-garment trouser system that includes a leg pant zipper (U.S. Pat. No. 5,057,094) for easy emptying of urine from the leg bag.

When wearing the disclosed undergarment pant, it appears to be just an ordinary opaque, stretch undergarment. The whole condom, tubing and leg bag are concealed within the external collection system. Some suggested stretchable materials the undergarment can be made with are cotton/poly/spandex blend or nylon/Tactel/LYCRA blend. The nylon/Tactel/LYCRA blend is a heavier fabric and can be used as an undergarment sport version of the pant system for higher intensity of activities. The cotton/poly/spandex-type blend is more suited for an underwear undergarment pant for daily use. The undergarment pant may vary in length to knee or mid-calf or ankle. Any length of the undergarment pant will hide and contain external collection urology system including condom, tubing and leg bag. There is a sewn-in expandable inner pocket made from the same material as the undergarment. This inner pocket can be on one leg of the undergarment pant or can be on both legs. This will allow for the user to change from leg to leg and it will also allow for some users with an ileoconduit or nephrostomy collection system to choose the more convenient leg to house the leg bag. The inner pocket consists of one piece of fabric and is sewn to the inside of the undergarment pant. The undergarment pant includes an opening (approximately 5" in vertical length) near the pelvic area for inserting and removing the leg bag. When the pouch is constructed for the outer leg position of the leg bag, this opening is positioned on the center seam of the undergarment pants. There is a small opening at the bottom of the inner pouch that allows the release valve to be placed through for easy elimination of urine from the leg bag while the user is wearing the undergarment pant. For the pouch to be positioned at the inner side of the leg, the pouch is sewn to the undergarment pant by two vertical seams which may include: one seam being the center front and continuing down the inner leg seam of the undergarment pant; and a second vertical seam sewn down the front of the leg. For the pouch to be positioned at the outer side of the leg, the pouch is sewn to the undergarment pant by two vertical seams which may include: one seam being the side seam of the undergarment and the second vertical seam sewn down the middle of the leg. The width of the pouch may vary. The bottom seam is sewn at the bottom hem of the undergarment pant and includes a small opening for the release valve. The top seam of the pouch is sewn into the elastic waistband of the undergarment pant. The stretchable pelvic area of the undergarment pant allows room for the male condom or the female device. The construction of this undergarment pant utilizes the strength of structural seams to hold the weight of the collection bag after is has been filled with urine discharge. After placing the leg bag in the inner pouch with the connected tubing attached, the user simply connects the tubing to the condom or female device through the opening at the pelvic area. The tubing can be shortened to fit the length between the condom/female device and the leg bag. The stretchable material of the undergarment pant further holds the whole external collection system in its proper place.

To keep the urine discharge from moving up the tubing of the external collection system contained in the undergarment pant and causing a leakage or accident, a one-way valve in the leg bag is recommended. This valve can be pressure related and can be positioned in the receiving tube or at the entry into the collection leg bag. The two connections at the ends of the tube can be the conventional overlap type or may include an overlap with a male/female screw connection. The leg bag includes a release valve on the lower edge to remove the liquid. The outlet valve located at the lower opening of the leg bag that may include a clamp-equipped discharge tube that can be fabricated with rigid plastic material. This valve is place through the lower opening in the inner leg pouch of the undergarment pant. The user easily releases the liquid through the release valve without having to remove the undergarment pant.

The undergarment pant system disclosed here is very simple to use. Attach the tube to the receiving nozzle of the collection leg bag and place the leg bag inside the inner leg pouch of the undergarment pant through the opening at the pelvic area. Position the release valve on the leg bag through the bottom opening in the inner leg pouch. Secure the condom sheath for male users or attach the external female device for female users and put on the undergarment pant. Attach the tube to the condom sheath or female device. The external collection system will be fully contained and concealed within the undergarment pant. Once the external collection system housed in the undergarment pant has received urine discharge, the user simply releases the urine from the leg bag by opening the release valve located at the bottom of the leg bag and positioned through the lower opening of the inner leg pouch in the undergarment pant. After urine release is complete, the user closes the valve.

For persons using this undergarment pant with ileoconduit or nephrostomy systems there are additional small opening positioned for the tubing. For ileoconduit systems where the tube comes from the bladder in the abdomen area, the undergarment pant includes a small opening located near the abdomen area for inserting the tube to attach to the leg bag contained in the undergarment pant. For the nephrostomy systems where the tube comes from the kidney area on the backside of the user, the undergarment pant includes a small opening at the top outer edge of the inner pouch for inserting the tube to attach to the leg bag contained in the undergarment pant.

Persons performing activities where the elimination of urine is restricted, limited or eliminated can also wear the disclosed undergarment pant. Some of these activities may include: pilots on long missions, tank drivers, long haul truckers, surgeons, climbers, firemen, security and rescue workers, and sport spectators.

The disclosed undergarment urine collection system can accommodate any size, shape and gender by making different sizes of the undergarment pant. (e.g. small, medium, large, extra large, etc.)

In accordance with an illustrated embodiment of the present invention, an undergarment pant extends on both legs from the waist to the knee area. In another embodiment, the undergarment pant length may extend to the calf or ankle. The invention includes a pouch sewn into one or both of the legs of the undergarment pant. The pouch may extend from the waistband to the hem of the pant and maybe sewn by two vertical seams, the elastic waistband and the lower hem seam. The vertical seams may include at least one structural seam including a side seam or center seam that continues down the inner leg towards the hem seam.

The invention holds and conceals the external collection urology system that includes condom, tube and leg bag without the need for leg straps on the leg bag. The invention includes arrangement for permitting insertion of the leg bag through an opening into the leg pouch that is sewn into the undergarment pant leg, preferably on the inside of the pant leg. The invention includes arrangements for permitting location of the release valve for the leg bag through a small opening sewn at the bottom of the pouch of the undergarment pant; this allows the user to empty the urine discharge without having to remove the undergarment pant. The undergarment pant is made from expandable material that provides for the expansion of the leg bag when urine discharge is released into the leg bag.

The undergarment pant may include a small opening for a tube from the bladder area when an ileoconduit system is used. The undergarment pant may also include a small opening for a tube coming from the backside near the kidney(s) of the user when a nephrostomy system is used.

In accordance with the present invention, another embodiment includes an external collection system for female users. The female system includes a female device positioned over the urethra and means for the tube to be attached. The tube allows urine discharge to move from the female device through the tube and into the leg bag.

OBJECTS AND ADVANTAGES

Accordingly, there are several objects and advantages to my invention, and certain of these are:
1. to provide arrangements for holding the external collection urology system in place without the use of leg straps;
2. to provide arrangements for a user to conceal the whole external collection urology system thereby helping to maintain their dignity;
3. to provide an easily accessible invention for users which is comfortable and easy to use;
4. to provide an invention that will permit the user a higher degree of physical activity without the external collection system becoming disengaged and causing a leakage or urinary accident;
5. to provide a better means for the ileoconduit and nephrostomy system users;
6. to provide an alternative to wearing diapers due to urinary incontinence;
7. to provide an external collection urology system that can be used by all age groups;
8. to provide an external collection urology system that can be used by ambulatory, paraplegic, quadriplegic and non-ambulatory person;
9. in addition, to provide a paraplegic or quadriplegic means for containing the leg bag inside their clothing and not having to wear the leg bag outside attached to their wheelchair.

Further advantages will become apparent from a consideration of the following description and the accompanying drawings.

DETAILED DESCRIPTION OF PREFERRED EMBODIMENTS

Figure 1:
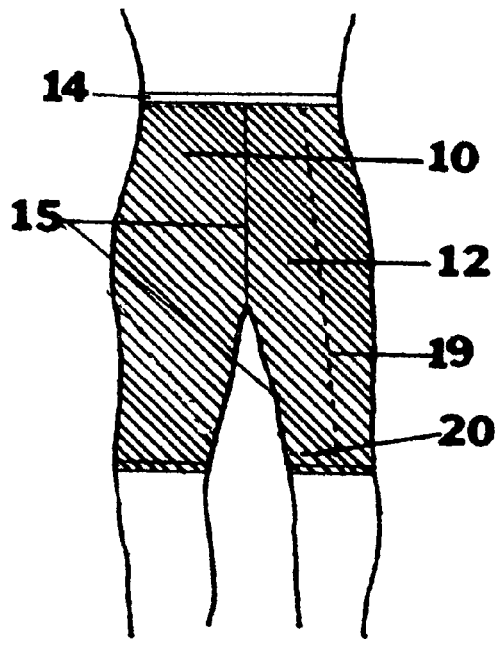
FIG. 1 is a front view of the undergarment pant system showing seams of inner leg pouch.
Figure 2:
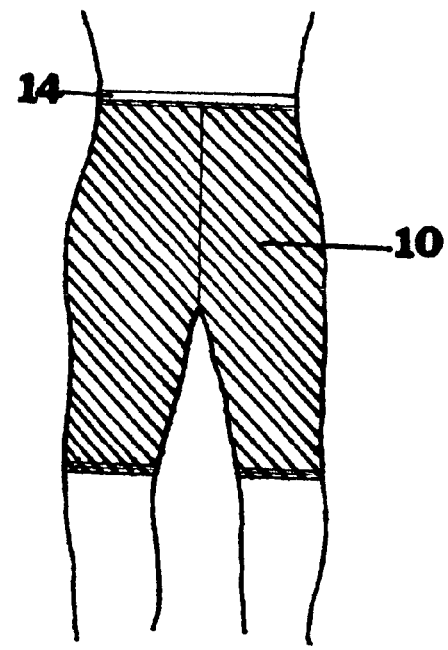
FIG. 2 is a back view of the undergarment pant.
Figure 3:
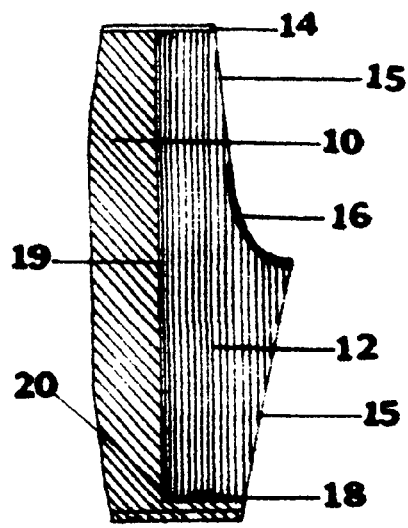
FIG. 3 is a front section of the undergarment pant including an inner leg pouch.
Figure 4:
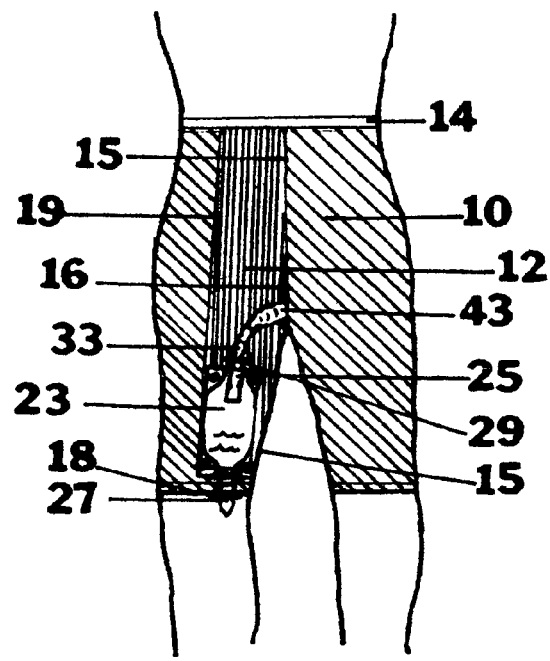
FIG. 4 is a front view of the undergarment pant showing the urine collection system of condom, tube and leg bag in relation to inner leg pouch.
Figure 6:
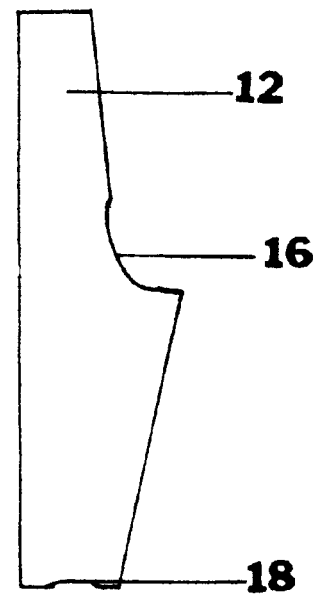
FIG. 6 is a view showing the inner leg pouch.
Figure 7:
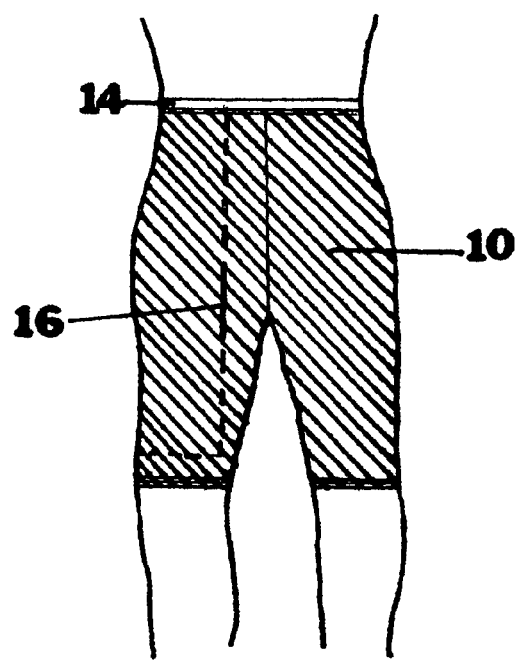
FIG. 7 is a front view of the undergarment showing the inner pouch on the outer front thigh.

An undergarment pant system (FIG. 1; FIG. 2; FIG. 4) for urinary collection is disclosed that can be worn by male and female users who are experiencing urinary incontinence, bladder or kidney disease that blocks the discharge. Persons performing activities where urine elimination is restricted or eliminated can also wear the undergarment pant. 10. The urine collection system includes an undergarment pant 10 made of stretchable, elastic-type fabric that may include fabric blends such as cotton/poly/Spandex® or Nylon® Tactel® & LYCRA®. The undergarment pant 10 includes an inner leg pouch on one leg (FIG. 3) of the undergarment pant 10 that is sewn into structural seams on the center front seam 15 and the elastic waistband 14 for strength and support. The center front seam 15 contains an opening 16 at the pelvic area that allows the leg bag 23 to be put into or out of the inner leg pouch 12. The inner leg pouch's 12 outer seam 19 is sewn down the middle of the leg of the undergarment pant 10 or can be sewn to the outside seam (FIG. 7). The lower seam 20 of the inner leg pouch 12 is located near the bottom hem of the undergarment pant 10 and includes a small opening 18 for the urine release valve 27 located at the lower edge of the urine bag 23.

Figure 5:
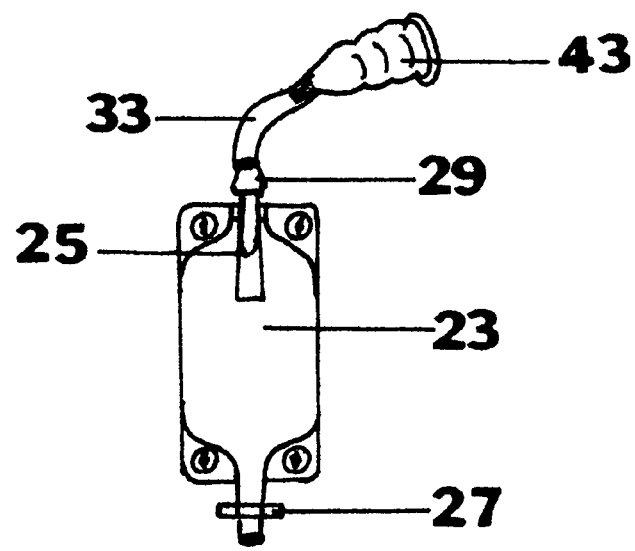
FIG. 5 is a view of the condom sheath, tube and leg bag that includes the receiving connection, exit connection and release valve.

The undergarment pant 10 includes an elastic waistband 14 and an inner leg pouch 12. The undergarment pant 10 hides the external collection system (FIG. 4; FIG. 5) that includes a condom 43 for men or a female device for female users, tube 33 and leg bag 23 for urine collection. The condom 43 or female device is hidden under the undergarment pant 10 in the pelvic area. The tube 33 and leg bag 23 are hidden within the inner leg pouch 12. The undergarment pant 10 can be knee length, calf length or ankle length and made of an elastic and expandable material. The inner leg pouch 12 is constructed to expand and it allows for the leg bag 23 to expand when retaining urine collection.

To keep the urine discharge from moving up in the tubing 33 in the urine collection system (FIG. 5), a one-way valve 25 is recommended. The one-way valve 25 can be pressure sensitive and can be positioned in the receiving tube 33 or at the entry 29 into the urine leg bag 23. The inner leg pouch 12 includes a small slit 18 at the bottom of the inner leg pouch 12 allowing the user to remove the drainage nozzle 27 and release the urine discharge from the leg bag 23. The attachments to the ends of the tubing 33 can be the conventional overlap type or may include an overlap with a male/female screw connection. Once the leg bag 23 is emptied, the release nozzle 27 can be easily replaced inside the bottom of the leg of the undergarment pant 10 through the lower opening 18. The undergarment 10 does not need to be removed to release the urine discharge from the leg bag 23.

Figure 8:
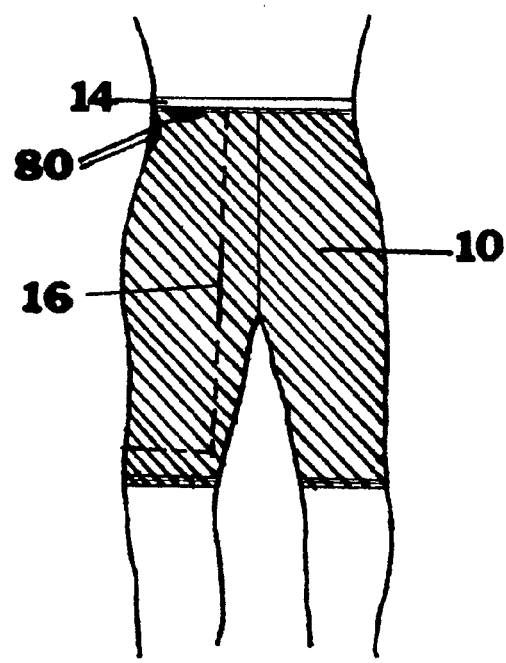
FIG. 8 is a front view of the undergarment showing small opening for the tube of a nephrostomy system.

The undergarment pant 10 can be used with a nephrostomy system (FIG. 8) having small opening 80 that allows the tube 33 to come around from the backside of the user and enter through a small opening 80 and allowing the tube to be connected to the leg bag 23 positioned within the inner pouch 12 in the undergarment 10.

The undergarment pant 10 disclosed here is very simple to use. Attach the tube 33 to the receiving nozzle 29 on the leg bag 23 and place the leg bag 23 inside the inner leg pouch 12 through the slit 16 on the center seam 15 near the pelvic area. Once the leg bag 23 is positioned at the bottom of the inner leg pouch 12, position the release valve 27 through the small opening 18 on the bottom seam 20. Secure the external condom 43 for male users or attached the external collection system for female users. Pull on the undergarment pant 10. Bring the other end of the tube 33 towards the pelvic slit 16 and attached the tube 33 to the condom sheath 43 or the female device. Pull the undergarment pant 10 towards the waist. The elastic-type material allows easy adjustment and positioning the penis or female urethra device within the pelvic area. Once the undergarment pant 10 and the urine collection system (FIG. 5) are in place, and the user receives urine in the leg bag 23, to simply release the urine from the leg bag 23 bring the release valve 27 through the small slit 18 at the bottom of the inner leg pouch 12. The user opens the release valve 27 and drains the fluid from the leg bag 23. After drainage is completed, the user closes the release valve 27 and replaces it inside the undergarment pant 10.

Operation of the System

The manner of using this invention is quite simple. First of all, place the leg bag inside the inner pouch. This can be done either by turning the undergarment inside out or keeping it right side out. Make sure the leg bag lays flat in the inner pouch. Place the release valve through the lower opening in the inner pouch. Connect the tubing to the leg bag that is placed in the inner pouch. To get the correct length of the tube, measure the length of the tubing to fit between the receiving valve on the leg bag and the condom sheath or the female external device; then add 1"–3" and cut the tubing to this length. Put the condom sheath or the female device on. If the undergarment has been turned inside out, turn it right side out, then pull the undergarment onto the body and connect the tubing to condom sheath or female device connector.

CONCLUSION AND RAMIFICATIONS

Thus the reader will see that this invention provides a very convenient and simple solution to a vast growing population having urinary problems and incontinence. The growing problem has been acknowledged and emphasized within the urology field. The simplicity of this invention allows for this to be a very reasonable and economical undergarment. Furthermore, it has the additional advantages in that:

it is not limited to one age group but allows children as well as adults to benefit from its use;
it is economically accessible to the consumer;
it does not restrict circulation to the leg;
it conceals the whole external collection urology systems thereby helping to maintain the users dignity;
it is comfortable and easy to use;
it permits the user to have a higher degree of physical activity without the external collection system becoming disengaged and causing a leakage or urinary accident;
it provides a better means for the ileoconduit and nephyrostomy system users;
it provides an alternative to wearing diapers due to urinary incontinence.

While the above description contains specifications, these should not be construed as limitations on the scope of the invention. Thus, by way of example but not of limitation, the pocket or pouch may be mounted on the outside of the thigh rather than in the preferred location on the inside of the thigh; and the pouch may extend to the lower hem of the undergarment, but may not be limited to the thigh area, particularly when longer undergarments below the knee, are worn. Accordingly, the scope of the invention should be determined not by the embodiment illustrated, but by the appended claims and their legal equivalents.

I claim:

1. A convenient system for collecting urine comprising: an undergarment extending around the waist and down both thighs of the user and having a crotch area and lower edges; said undergarment not comprising restricting elastic straps or bands for securing the urine collection leg bag around the circumference of a leg; a pouch formed of an additional piece of fabric sewn to the inside of the undergarment for securing the urine collection leg bag, said inside pouch extending along the thigh of the user and being located wholly within the undergarment above the lower edges thereof; said undergarment comprising a sewn structural seam attaching the outer edge of the pouch to the undergarment, said sewn seam extending from an elastic waistband to lower seam edge of pant leg; said undergarment comprising a sewn structural seam attaching the inner edge of the pouch to the undergarment, said sewn seam extending from an elastic waistband to a crotch area and down the inner thigh seam of the leg to the leg hem; said undergarment comprising a sewn structural seam attaching the bottom edge of the inner pouch to the undergarment at the leg hem; said structural seams not comprised of elastic straps or bands; a urine collection leg bag supported in said pouch; said leg bag having an outlet release valve; said undergarment having a small opening at the bottom of the pouch to receive said outlet release valve; said pouch extending from the waist area down the thighs; and said pouch further having an opening at the crotch area, for receiving the urine collection leg bag; and urine collection arrangements connected from the user's crotch area to the urine collection leg bag.

2. A system as defined in claim 1 wherein said urine collection arrangements include a condom-like coupling for male users.

3. A system as defined in claim 1 wherein said urine collection arrangements include an external receiving device for female users.

4. A system as defined in claim 1 wherein said urine collection arrangements include a tube to connect the leg bag to the condom-like coupling for male users or an external receiving device used by female users.

5. A system as defined in claim 1 wherein the materials for the undergarment are stretchable; and the materials for the laminar-type leg bag may include expandable plastic, latex, rubber or other plastic material.

6. A system as defined in claim 1 wherein the release valve of the leg bag may be positioned below the lower edge of the undergarment or may be positioned on the inside of the lower edge of the undergarment.

7. A system as defined in claim 1 wherein a small opening is provided to receive a tube to the inside of the undergarment for attaching said tube to the leg bag placed in the pouch when using a nephrostomy system.

8. A system as defined in claim 1 wherein the pouch can be sewn at the inner front thigh or at the outer front thigh.

9. A system as defined in claim 1 wherein the undergarment can be extended below the knee to the lower leg.

10. A convenient system for collecting urine comprising: an undergarment extending around the waist and down both thighs of the user and having lower edges; said undergarment not comprising restricting elastic straps or bands for securing the urine collection leg bag around the circumference of a leg; a pouch formed of an additional piece of fabric sewn to the inside of the undergarment for securing the urine collection leg bag, said inside pouch extending along the thigh of the user and being located wholly within the undergarment above the lower edges thereof; said undergarment comprising a sewn structural seam attaching the outer edge of the pouch to the undergarment, said sewn seam extending from an elastic waistband to a lower seam edge of a pant leg; said undergarment comprising a sewn structural seam attaching the inner edge of the pouch to the undergarment, said sewn seam extending from an elastic waistband to a crotch area and down the inner thigh seam of the leg to the leg hem; said undergarment comprising a sewn structural seam attaching the bottom edge of the inner pouch to the undergarment at the leg hem; said structural seams not comprised of elastic straps or bands; a urine collection leg bag supported in said pouch; said leg bag having an outlet release valve; said pouch or undergarment having a small opening at the bottom thereof to receive said outlet release valve; the pouch extending down the thighs; and the pouch further having an opening at the crotch area for receiving the urine collection leg bag; and urine collection arrangements connected from the user's crotch area to the urine collection leg bag.

11. A system as defined in claim 9 wherein said urine collection arrangements include a condom-like coupling for male users.

12. A system as defined in claim 9 wherein said urine collection arrangements include an external receiving device used by female users.

13. A system as defined in claim 9 wherein said urine collection arrangements include a leg bag and a tube to connect the leg bag to the condom-like coupling for male users or an external receiving device used by female users.

14. A system as defined in claim 9 wherein the materials for the undergarment are stretchable and may include a woven cotton/spandex blend, a nylon/LYCRA, or any variables of stretchable materials; and the materials for the laminar-type leg bag may include expandable plastic, rubber or thermoplastic material.

15. A system as defined in claim 9 wherein the release valve of the leg bag may be positioned below the lower edge of the undergarment or may be positioned on the inside of the lower edge of the undergarment.

16. A system as defined in claim 9 wherein a small opening to receive a tube to the inside of the undergarment, and attaching said tube to the leg bag placed in the pouch when using a nephrostomy system.

17. A system as defined in claim 9 wherein the pouch can be sewn at the inner front thigh or at the outer front thigh.

18. A system as defined in claim 9 wherein the undergarment can be extended below the knee to the lower leg.

19. A convenient method for collecting urine using the system according to claim 1, comprising the steps of: forming an undergarment, fabricated from woven stretchable fabric, extending around the waist and down both thighs of the user and having lower edges, and including an inside pouch formed of an additional piece of fabric sewn along the thigh of the user and being located wholly within the undergarment above the lower edges; and not comprising restricting elastic straps or bands for securing the urine collection leg bag but comprising sewn structural seams from an elastic waistband to a lower seam edge of a pant leg and a sewn structural seam connecting the bottom edge of said inside pouch to the leg hem for securing the urine collection leg bag on the users leg thereof; for (a) placing a urine collection leg bag with said pouch through an opening in the crotch area;

(b) directing urine from the urethra area, through a tube that is connected to the leg bag;

(c) receiving an outlet release valve from the leg bag through a small opening at the bottom of the pouch.

20. A method as defined in claim 19 comprising the additional steps of connecting a tube from a nephrostomy system by means of a small opening in the undergarment permitting the tube to enter the inner pouch, and connecting said tube to said leg bag.

* * * * *